(12) United States Patent
Yasui et al.

(10) Patent No.: US 11,717,157 B2
(45) Date of Patent: Aug. 8, 2023

(54) VISUAL SENSE EXAMINATION DEVICE

(71) Applicant: QD LASER, INC., Kawasaki (JP)

(72) Inventors: Kenji Yasui, Kawasaki (JP); Makoto Suzuki, Kawasaki (JP); Mitsuru Sugawara, Kawasaki (JP); Kinya Hasegawa, Kawasaki (JP)

(73) Assignee: QD LASER, INC., Kawasaki (JP)

( * ) Notice: Subject to any disclaimer, the term of this patent is extended or adjusted under 35 U.S.C. 154(b) by 613 days.

(21) Appl. No.: 16/650,798

(22) PCT Filed: Sep. 12, 2018

(86) PCT No.: PCT/JP2018/033824
§ 371 (c)(1),
(2) Date: Mar. 25, 2020

(87) PCT Pub. No.: WO2019/069648
PCT Pub. Date: Apr. 11, 2019

(65) Prior Publication Data
US 2020/0229694 A1 Jul. 23, 2020

(30) Foreign Application Priority Data
Oct. 5, 2017 (JP) .................. 2017-195447

(51) Int. Cl.
*A61B 3/10* (2006.01)
*A61B 3/12* (2006.01)
(Continued)

(52) U.S. Cl.
CPC .......... *A61B 3/1225* (2013.01); *A61B 3/0025* (2013.01); *A61B 3/0058* (2013.01);
(Continued)

(58) Field of Classification Search
CPC ... A61B 3/1225; A61B 3/0025; A61B 3/0058; A61B 3/0091; A61B 3/024;
(Continued)

(56) References Cited

U.S. PATENT DOCUMENTS 4,620,318 A 10/1986 Hill
4,968,130 A 11/1990 Hideshima
(Continued)

FOREIGN PATENT DOCUMENTS

CN 103750814 A 4/2014
EP 0738123 A1 10/1996
(Continued)

OTHER PUBLICATIONS

Extended European Search Report for European Patent Application No. 18864830.7 dated Aug. 6, 2020 (5 sheets).
(Continued)

*Primary Examiner* — Mahidere S Sahle
(74) *Attorney, Agent, or Firm* — Kratz, Quintos & Hanson, LLP

(57) ABSTRACT

A visual sense examination device includes: a beam source that emits a visible beam and an invisible beam; a visible beam optical system that includes a first scanner scanning the visible beam; an invisible beam optical system that includes a second scanner scanning the invisible beam; a detector that detects the invisible beam reflected by a retina of a subject; a controller that performs a first control; a synthesizer that synthesizes the visible beam scanned by the first scanner and the invisible beam scanned by the second scanner; and wherein scanning angles of the visible beam by the first scanner and the invisible beam by the second scanner are substantially the same, and projectable ranges of the visible beam scanned by the first scanner and the
(Continued)

invisible light scanned by the second scanner are substantially the same on the retina of the subject.

13 Claims, 15 Drawing Sheets

(51) Int. Cl.
*A61B 3/00* (2006.01)
*A61B 3/024* (2006.01)

(52) U.S. Cl.
CPC .............. *A61B 3/0091* (2013.01); *A61B 3/024* (2013.01); *A61B 3/1025* (2013.01)

(58) Field of Classification Search
CPC ......... A61B 3/1025; A61B 3/102; A61B 3/14; A61B 3/12; A61B 2018/207
USPC .......................................... 351/206, 211, 221
See application file for complete search history.

(56) References Cited

U.S. PATENT DOCUMENTS

| | | | |
|---|---|---|---|
| 5,620,000 A | | 4/1997 | Zinser |
| 2005/0286019 A1 | | 12/2005 | Wiltberger |
| 2007/0291277 A1 | | 12/2007 | Everett |
| 2011/0199579 A1 | * | 8/2011 | Muto ...................... A61B 3/14 351/208 |
| 2012/0002167 A1 | | 1/2012 | Kondoh |
| 2015/0313467 A1 | | 11/2015 | Sakai |
| 2016/0371836 A1 | * | 12/2016 | Kuno .................... G06T 11/008 |
| 2018/0206716 A1 | | 7/2018 | Chong |
| 2018/0242839 A1 | * | 8/2018 | Fukuhara ............... A61B 3/102 |

FOREIGN PATENT DOCUMENTS

| | | |
|---|---|---|
| JP | S59-200628 A | 11/1984 |
| JP | H01-113025 A | 5/1989 |
| JP | 2007-181537 A | 7/2007 |
| JP | 2010-110391 A | 5/2010 |
| JP | 2010-259606 A | 11/2010 |
| JP | 2012-011146 A | 1/2012 |
| JP | 2013-119019 A | 6/2013 |
| KR | 101422731 B1 * | 7/2014 |
| WO | 2014/084231 A1 | 6/2013 |
| WO | 2016/196463 A1 | 12/2016 |

OTHER PUBLICATIONS

International Preliminary Report on Patentability for International Application No. PCT/JP2018/033824 dated Jun. 19, 2019 (23 sheets translation).
Office Action of corresponding Japanese Patent Application No. 2020-044352 dated Oct. 5, 2021 (4 sheets, 4 sheets translation, 8 sheets total).
Office Action of counterpart Japanese Patent Application No. 2020-044352 dated Mar. 9, 2021 (5 sheets, 5 sheets translation, 10 sheets total).
Office Action of counterpart Japanese Patent Application No. 2019-546602: Notification of Reasons for Refusal dated Nov. 19, 2019 (10 sheets, 9 sheets translation, 19 sheets total).
International Search Report for International Application No. PCT/JP2018/033824 dated Nov. 20, 2018 (3 sheets, 2 sheets translation, 5 sheets total).
Written Opinion of the International Preliminary Report on Patentability for International Application No. PCT/JP2018/033824 dated Mar. 19, 2019 (12 sheets).
International Preliminary Report on Patentability for International Application No. PCT/JP2018/033824 dated Jun. 19, 2019.
Office Action of counterpart Japanese Patent Application No. 2019-546602: Decision to Grant a Patent dated Feb. 18, 2020 (3 sheets, 2 sheets translation, 5 sheets total).
Extended European Search Report for corresponding European Patent Application No. 18864830.7 dated Oct. 19, 2020 (5 sheets).
Communication pursuant to Article 94(3) EPC of corresponding European Patent Application No. 18864830.7 dated Sep. 7, 2022 (4 sheets).

* cited by examiner

VISUAL SENSE EXAMINATION DEVICE

TECHNICAL FIELD

The present invention relates to a visual sense examination device.

BACKGROUND ART

There has been known fundus examination using a scanning laser ophthalmoscope (SLO). Also, there has been known an ophthalmologic apparatus provided with functions of the scanning laser ophthalmoscope and perimetry.

PRIOR ART DOCUMENTS

Patent Document

Patent Document 1: Japanese Patent Application Publication No. 2007-181537

SUMMARY OF THE INVENTION

Problem to be Solved by the Invention

With respect to an examination device capable of emitting an invisible beam to a retina of a subject and projecting an image on the retina for an eye examination, when the image is displayed using a liquid crystal display as in Patent Document 1, it is difficult to project a high-resolution image on the retina.

The present invention has been made in view of the above problem, and aims to provide a visual sense examination device that can project a high-resolution image.

Means for Solving the Problem

The present invention is a visual sense examination device including: a beam source that emits a visible beam and an invisible beam; a visible beam optical system that includes a first scanner two-dimensionally scanning the visible beam, and that emits the visible beam to a retina of a subject; an invisible beam optical system that includes a second scanner two-dimensionally scanning the invisible beam, and that emits the invisible beam to the retina of the subject: a detector that detects the invisible beam reflected b the retina of the subject; a controller that performs a first control, the first control including: controlling the emission of the visible beam from the beam source, and causing the first scanner to scan the visible beam for an image for projecting the image and to emit the visible beam for the image to the retina of the subject; controlling the emission of the invisible beam from the beam source. and causing the second scanner to scan the invisible beam for detecting a state of a fundus of the subject and to emit the invisible beam to the retina of the subject: and acquiring a first fundus image of an eye of the subject from an output signal of the detector based on the invisible beam for detecting the state of the fundus of the subject, a synthesizer that synthesizes the visible beam scanned by the first scanner and the invisible beam scanned by the second scanner; wherein a scanning angle of the visible beam by the first scanner d a scanning angle of the invisible beam by the second scanner are substantially the same, and a projectable range of the visible beam scanned two-dimensionally by the first scanner and a projectable range of the invisible light scanned two-dimensionally by the second scanner are substantially the same on the retina of the subject.

In the above configuration, the visible beam optical system and the invisible beam optical system share a first lens that is disposed between the synthesizer and the eye of the subject and converges the visible beam scanned by the first scanner and the invisible beam scanned by the second scanner inside the eye of the subject, the visible beam optical system includes a second lens disposed between the first scanner and the synthesizer, and guiding the visible beam scanned by the first scanner to the synthesizer, and the invisible beam optical system includes a third lens disposed between the second scanner and the synthesizer, and guiding the invisible beam scanned by the second scanner to the synthesizer.

In the above configuration, the visual sense examination device includes: a spectroscope that emits the visible beam emitted from the beam source in a first direction, and emits the invisible beam emitted from the beam source in a second direction different from the first direction: wherein the visible beam optical system two-dimensionally scans thy: visible beam emitted in the first direction to emit the visible beam to the retina of the subject, the invisible beam optical system two-dimensionally scans the invisible beam emitted in the second direction to emit the invisible beam to the retina of the subject, the detector detects the invisible beam reflected by the retina of the subject, the invisible beam passing through the synthesizer the second scanner and the spectroscope.

In the above configuration, optical axes of the visible beam and the invisible beam from the beam source to the spectroscope match, and the optical axes thereof from the synthesizer to the retina of the subject match.

In the above configuration, the spectroscope is a dichroic mirror that transmits one of the visible beam and the invisible beam, and reflects the other thereof.

In the above configuration, the invisible bean is an infrared beam.

In the above configuration, the controller causes the beam source to emit the invisible beam for detecting the state of the fundus of the subject, the controller projects, on the retina of the subject, a fixation visual target for directing a visual line of the subject by the visible beam for the image.

In the above configuration, the controller projects an examination visual target for examining an eye of the subject on the retina of the subject by the visible beam for the image.

In the above configuration, the controller performs the projection of the examination visual target and the emission of the invisible beam in parallel.

In the above configuration, the controller projects a visual target for examining a visual field of the subject, as the examination visual target.

In the above configuration, the controller generates a superimposed image in which the first fundus image and a visual field defect image are superimposed, the visual field defect image being generated based on a response input in accordance with the examination visual target of the subject.

In the above configuration, the detector detects a visible beam for fundus examination for detecting the state of the fundus of the subject, and the invisible beam reflected by the a of the subject, the visible beam for fundus examination being reflected by the retina of the subject and different from the visible beam for the image, the controller performs a second control, the second control including: controlling the emission of the visible beam from the beam source to emit the visible beam for fundus examination to the retina of the subject: controlling the emission of the invisible beam from the beam source to emit the invisible beam for detecting the state of the fundus of the subject to the retina of the subject; acquiring a second fundus image of the eye of the subject from the output signal of the detector based on the visible beam for fundus examination: and acquiring a third fundus image of the eye of the subject from the output signal of the detector based on the invisible beam for detecting the state of the fundus of the subject.

The present invention is a visual sense examination device including: a visible beam source that emits a visible beam; an invisible beam source that emits an invisible beam; a beam source beam synthesizer that synthesizes the visible beam and the invisible beam to generate a synthesis beam; a scanner that two-dimensionally scans the visible beam and the invisible beam; an emission optical system that emits the visible beam to a retina of a subject to project an image on the retina of the subject, and emits the invisible beam to the retina of the subject; a detector that detects the invisible beam reflected by the retina of the subject; and a controller that controls the emission of the visible beam from the visible beam source and the invisible beam from the invisible beam source, controls the emission of the visible beam from the visible beam source to project a visual target on the retina of the subject, and generates a fundus image of an eye of the subject on which the visual target is projected, from an output signal of the detector, the fundus image including an image of the projected visual target.

In the above configuration, the visual target includes a fixation visual target for directing a visual line of the subject to the retina of the subject by the visible beam.

In the above configuration, the visual target includes an examination visual target for examining an eye of the subject projected on the retina of the subject the visible beam.

In the above configuration, the invisible beam is an infrared beam. In the above configuration, the controller performs the projection of the visual target and the emission of the invisible beam in parallel.

In the above configuration, the visual sense examination device includes an inputter that inputs operation by the subject, the controller generates a second examination image in which the fundus image generated based on the output signal of the detector and a first examination image generated based on a response input from the inputter in accordance with the examination visual target of the subject are superimposed.

In the above configuration, the first examination image is an image related to visual field defect.

Effects of the Invention

According to the present invention, it is possible to project a high-resolution image.

EMBODIMENTS FOR CARRYING OUT THE INVENTION

The following is a description of embodiments of the present invention, with reference to the drawings.

First Embodiment

Figure 1:
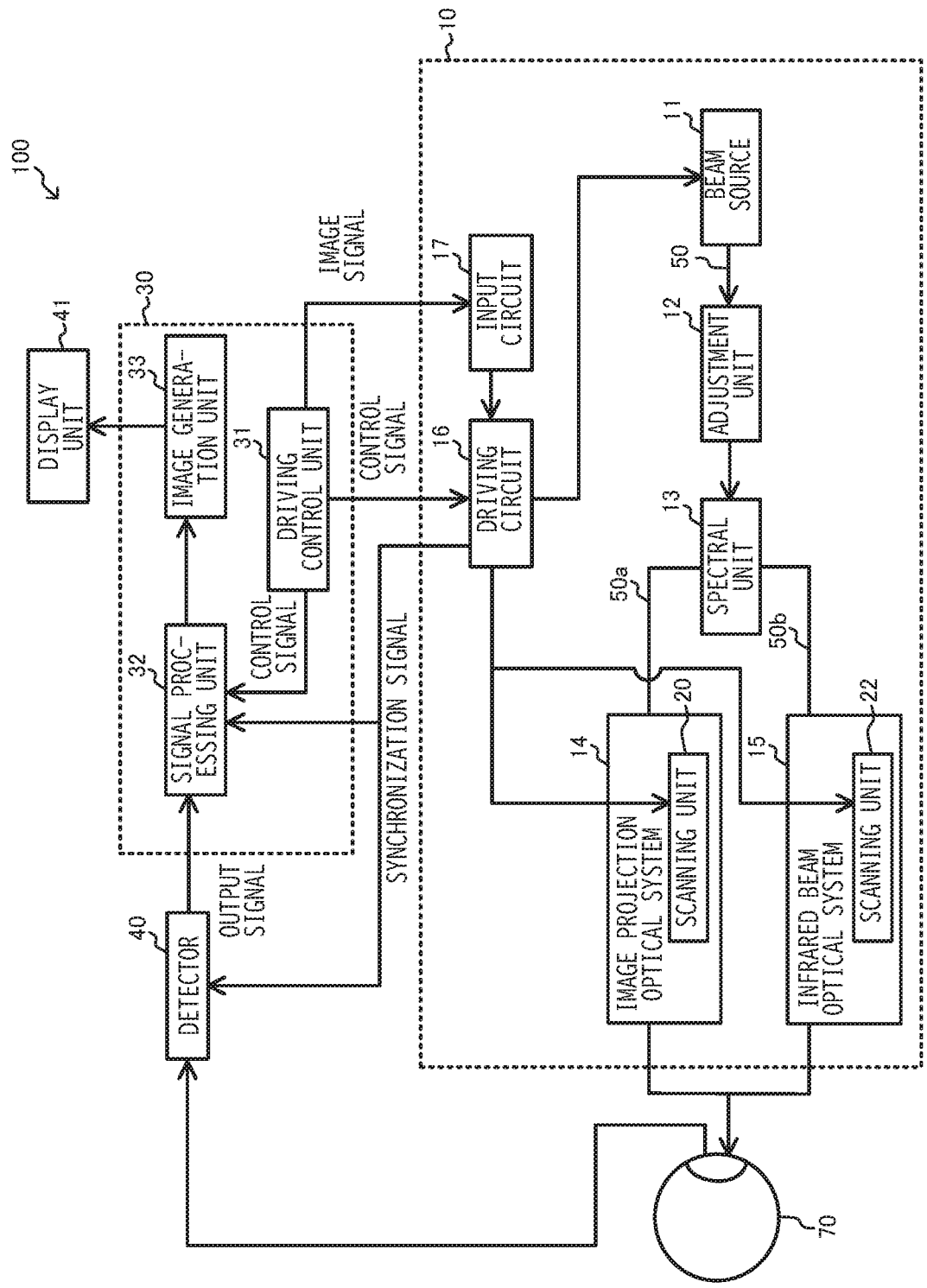
FIG. 1 is a block diagram of a visual sense examination device according to a first embodiment.

FIG. 1 is a block diagram of a visual sense examination device according to a first embodiment. As illustrated in FIG. 1, a visual sense examination device 100 according to the first embodiment includes a projection unit 10, a control unit 30, a detector 40 and a display unit 41. The projection unit 10 includes a beam source 11, an adjustment unit 12, a spectral unit 13, an image projection optical system 14, an infrared beam optical system 15, a driving circuit 16 and an input circuit 17. The image projection optical system 14 has a scanning unit 20, and the infrared beam optical system 15 has a scanning unit 22. The scanning units 20 and 22 (scanners) are scanning mirrors such as MEMS (Micro Electro Mechanical System) mirrors, or transmission type scanners, for example. The control unit 30 includes a driving control unit 31, a signal processing unit 32 and an image generation unit 33.

The driving control unit 31 generates an image to be projected on a retina or the like. An image signal is input from the driving control unit 31 to the input circuit 17. The driving circuit 16 drives the beam source 11 and the scanning units 20 and 22 based on the image signal obtained by the input circuit 17 and a control signal of the driving control unit 31.

The beam source 11 emits a visible beam such as a red laser beam (wavelength: about 610 nm to 660 nm), a green laser beam (wavelength: about 515 nm to 540 nm) and a blue laser beam (wavelength: about 440 nm to 480 nm), and an invisible beam which is an infrared laser beam (wavelength: about 850 nm), for example. That is, the beam source 11 has respective laser diode chips for the red laser beam, the green laser beam, the blue laser beam and the infrared laser beam in a single module. Here, the beam source 11 may emit a laser beam with a single wavelength as the visible beam.

The adjustment unit 12 has a collimate lens, a toric lens, and/or an aperture, and shapes a laser beam 50 emitted from the beam source 11. The laser beam 50 is a beam obtained by synthesizing the red laser beam, the green laser beam, a blue laser beam and/or the infrared laser beam, and the optical axes of the respective laser beams match each other. The spectral unit 13 is a dichroic mirror, for example, and spectrally disperses the laser beam 50 into a visible laser beam 50a including the red laser beam, the green laser beam and the blue laser beam, and an infrared laser beam 50b. The image projection optical system 14 two-dimensionally scans the visible laser beam 50a spectrally dispersed by the spectral unit 13 with the scanning unit 20 and emits the visible laser beam 50a to an eye 70 of a subject. The infrared beam optical system 15 two-dimensionally scans the infrared laser beam 50b spectrally dispersed by the spectral unit 13 with the scanning unit 22 and emits the infrared laser beam 50b to the eye 70 of the subject. The infrared beam optical system 15 realizes a part of functions of a conventional scanning laser ophthalmoscope (SLO), for example.

The detector 40 is a photodetector such as an avalanche photodiode, for example, and detects the infrared laser beam 50b reflected by the eye 70 of the subject. The signal processing unit 32 processes an output signal of the detector 40 based on a control signal from the driving control unit 31. The image generation unit 33 generates a two-dimensional image based on the signal processed by the signal processing unit 32. The display unit 41 is a liquid crystal display, for example, and displays the image generated by the image generation unit 33. The detector 40 and the signal processing unit 32 start the detection at the timing when the beam source 11 emits the infrared laser beam 50b, based on a synchronization signal from the driving circuit 16.

The driving control unit 31, the signal processing unit 32 and the image generation unit 33 may be a processor such as a CPU (Central Processing Unit) that performs processing in cooperation with a program. The driving control unit 31, the signal processing unit 32 and the image generation unit 33 may be circuits designed exclusively. The driving control unit 31, the signal processing unit 32 and the image generation unit 33 may be a single circuit or different circuits.

Figure 2:
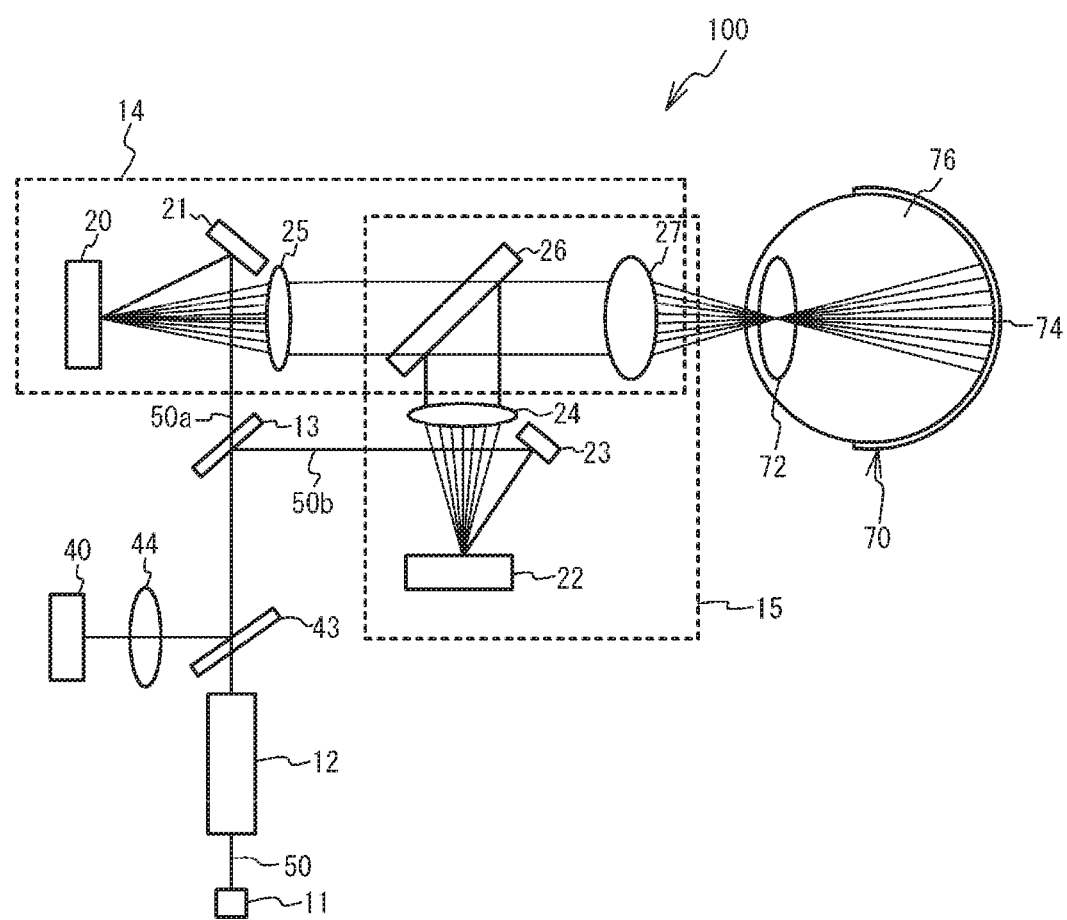
FIG. 2 is a diagram illustrating an optical system of the visual sense examination device according to the first embodiment.

FIG. 2 is a diagram illustrating an optical system of the visual sense examination device according to the first embodiment. As illustrated in FIG. 2, the visual sense examination device 100 according to the first embodiment emits the laser beam to the retina 74 of the subject using Maxwellian view. A numerical aperture (NA) and/or a beam diameter of the laser beam 50 emitted from the beam source 11 are adjusted by the adjustment unit 12. The laser beam 50 are spectrally dispersed into the visible laser beam 50a including the red laser beam, the green laser beam and the blue laser beam, and the infrared laser beam 50b in the spectral unit 13. The spectral unit 13 is the dichroic mirror that transmits the visible laser beam 50a and reflects the infrared laser beam 50b, for example. Here, the spectral unit 13 is not limited to the dichroic mirror, but may be another optical element such as a dichroic prism.

The visible laser beam 50a is reflected by a plane mirror 21 and is scanned two-dimensionally by the scanning unit 20. The scanned visible laser beam 50a is emitted to the eye 70 of the subject via a lens 25, a synthesis unit 26 and a lens 27. The visible laser beam 50a converges near a crystalline lens 72, passes through a vitreous body 76, and is emitted to the retina 74. Thereby, the image is projected on the retina 74. The scanning unit 20 oscillates at a relatively high frequency such as 28 kHz so that the images of 60 frames are projected per second, for example.

The infrared laser beam 50b is reflected by a plane mirror 23 and is scanned two-dimensionally by the scanning unit 22. The scanned infrared laser beam 50b is emitted to the eye 70 of the subject via the lens 25, the synthesis unit 26 and the lens 27. The infrared laser beam 50b converges near the crystalline lens 72, passes through the vitreous body 76, and is emitted to the retina 74. The infrared laser beam 50b is reflected by the retina 74. The reflected infrared laser beam 50b returns along an optical path where the infrared laser beam 50b has advanced toward the retina 74. That is, the reflected infrared laser beam 50b returns in an order of the lens 27, the synthesis unit 26, a lens 24, the scanning unit 22, the plane mirror 23 and the spectral unit 13, along the optical path where the infrared laser beam 50b has advanced toward the retina 74. Then, the reflected infrared laser beam 50b enters the detector 40 via a half mirror 43 and a lens 44. Thereby, the detector 40 detects the infrared laser beam 50b reflected by the retina 74. The state of a fundus of the eye 70 can be detected (state information of the fundus can be obtained) based on the detection result of the luminance change of the infrared laser beam 50b by the detector 40, and a fundus image can be obtained as an example of a detection object. The scanning unit 22 oscillates at a relatively low frequency such as 12.5 kHz, which corresponds to a case where the images of 25 frames are projected per second, so that the detection of the state of the fundus of the eye 70 can be realized by the infrared laser beam 50b.

Figure 3A:
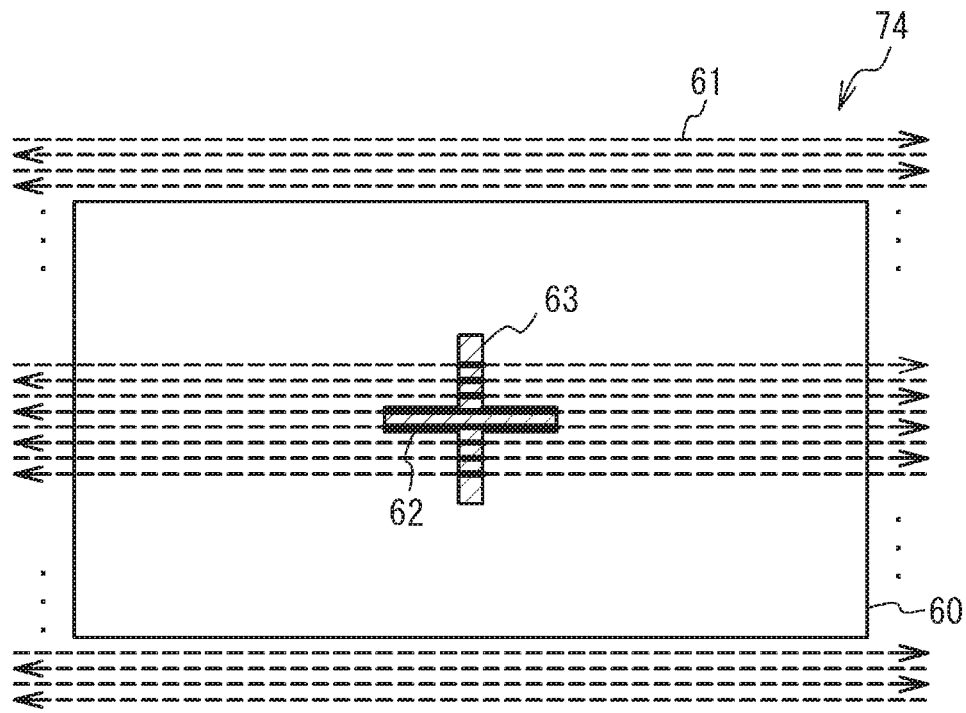
FIGS. 3A and 3B are diagrams illustrating the scanning of a visible laser beam and an infrared laser beam.
Figure 3B:
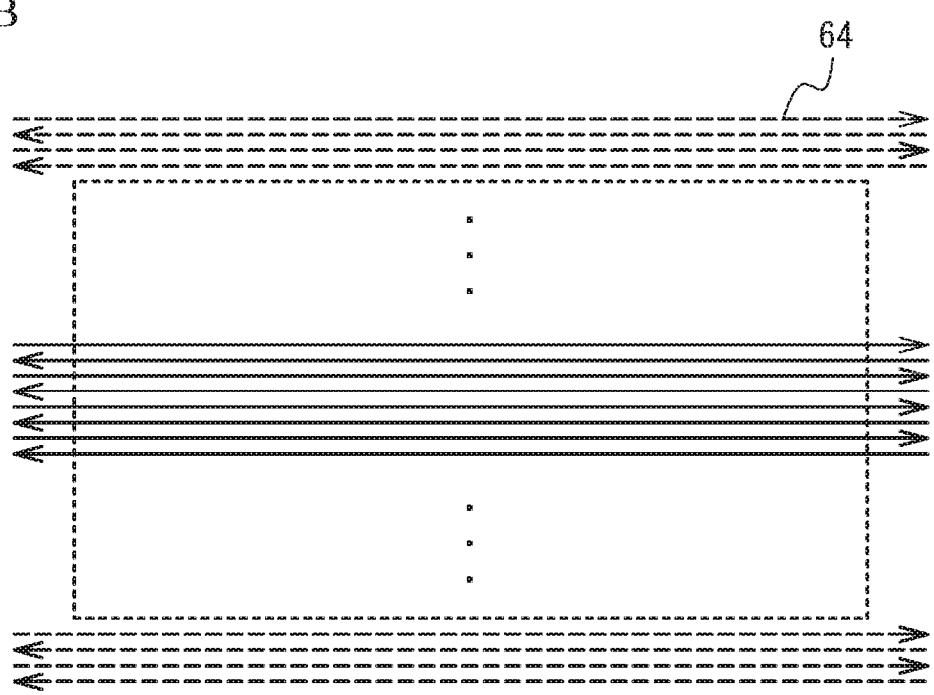

FIGS. 3A and 3B are diagrams illustrating the scanning of the visible laser beam 50a and the infrared laser beam 50b. As illustrated in FIG. 3A, the image 60 is projected on the retina 74 by the visible laser beam 50a. The scanning unit 20 of the image projection optical system 14 performs a raster scan of the visible laser beam 50a from an upper left to a lower right, as indicated by arrows 61. If the beam source 11 does not emit the visible laser beam 50a even when the scanning unit 20 oscillates, the visible laser beam 50a is not emitted to the retina 74. The visible laser beam 50a is not emitted at dashed arrows 61 of FIG. 3A. The driving circuit 16 synchronizes the emission of the visible laser beam 50a from the beam source 11 with the oscillation of the scanning unit 20. Thereby, the beam source 11 emits the visible laser beam 50a along thick solid lines 62. Accordingly, a fixation visual target 63 for directing a visual line of the subject is projected on a central region of the retina 74, for example. The fixation visual target 63 is not limited to a cross pattern, but may be other figure such as a dot pattern, a star pattern, a circular pattern or a polygonal pattern as long as the visual line of the subject can be directed. Also, a display position of the fixation visual target 63 is not limited to the central region of the retina 74, but may be changed as needed.

As illustrated in FIG. 3B, the scanning unit 22 of the infrared beam optical system 15 performs a raster scan of the infrared laser beam 50b from the upper left to the lower right, as indicated by arrows 64. If the beam source 11 does not emit the infrared laser beam 50b even when the scanning unit 22 oscillates, the infrared laser beam 50b is not emitted to the retina 74. The driving circuit 16 synchronizes the emission of the infrared laser beam 50b from the beam source 11 with the oscillation of the scanning unit 22. Even when the infrared laser beam 50b is emitted to the retina 74, the subject cannot recognize that the infrared laser beam 50b has been emitted because the infrared laser beam 50b is the invisible beam. The beam source 11 emits the infrared laser beam 50b in accordance with the oscillation of the scanning unit 22 in substantially the same range as the image 60, for example.

Returning to FIG. 2, a scanning angle of the visible laser beam 50a by the scanning unit 20 and a scanning angle of the infrared laser beam 50b by the scanning unit 22 are approximately the same size, for example. The synthesis unit 26 is the dichroic mirror, for example, and synthesizes the visible laser beam 50a scanned by the scanning unit 20 and the infrared laser beam 50b scanned by the scanning unit 22. After the visible laser beam 50a and the infrared laser beam 50b are synthesized by the synthesis unit 26, the optical axes thereof match each other. Here, the synthesis unit 26 is not limited to the dichroic mirror, but may be another optical element such as the dichroic prism.

The image projection optical system 14 includes the scanning unit 20, the plane mirror 21, the lens 25, the synthesis unit 26 and the lens 27. The infrared beam optical system 15 includes the scanning unit 22, the plane mirror 23, the lens 24, the synthesis unit 26 and the lens 27. The synthesis unit 26 and the lens 27 are common components in the image projection optical system 14 and the infrared beam optical system 15.

Figure 4:
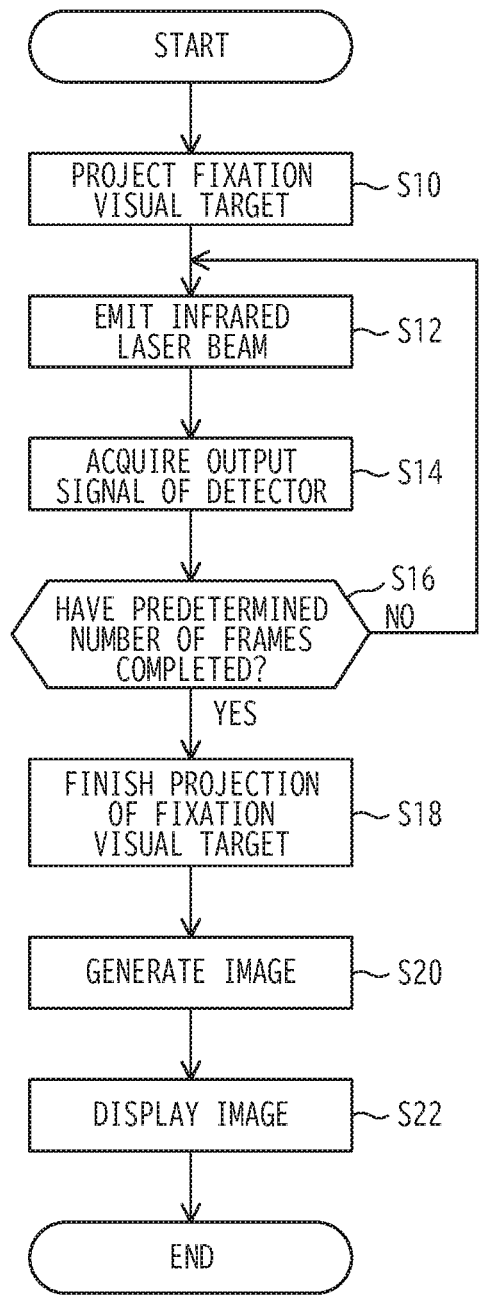
FIG. 4 is a flowchart illustrating processing according to the first embodiment.

FIG. 4 is a flowchart illustrating processing according to the first embodiment. As illustrated in FIG. 4, the driving control unit 31 generates an image 60 as illustrated in FIG. 3A, causes the projection unit 10 to project the generated image 60 and project the fixation visual target 63 on the retina 74 (step S10). Next, the driving control unit 31 causes the projection unit 10 to emit the infrared laser beam 50b to the retina 74, as illustrated in FIG. 3B (step S12).

Next, the signal processing unit 32 acquires an output signal of the detector 40 (step S14). For example, the detector 40 detects the infrared laser beam 50b in synchronization with the synchronization signal from the driving circuit 16. That is, the detector 40 detects the infrared laser beam 50b in synchronization with the emission of the infrared laser beam 50b from the beam source 11. The signal processing unit 32 starts acquiring the output signal of the detector 40 in synchronization with the emission of the infrared laser beam 50b.

Next, the driving control unit 31 determines whether the emission of the infrared laser beam 50b corresponding to a predetermined number of frames has completed (step S16). The predetermined number of frames may be one frame or a plurality of frames such as 5 frames or 10 frames. The number of frames suitable for detecting the state of the fundus of the eye 70 by emitting the infrared laser beam 50b to the retina 74 may be appropriately selected.

When the emission of the infrared laser beam 50b corresponding to the predetermined number of frames has not completed (step S16: No), steps S12 and S14 are repeatedly performed. When the emission of the infrared laser beam 50b corresponding to the predetermined number of frames has completed (step S16: Yes), the driving control unit 31 causes the projection unit 10 to finish the projection of the fixation visual target 63 (step S18).

Next, the image generation unit 33 generates an examination image (for example, a fundus image) of the eye 70 based on the output signal of the detector 40 acquired by the signal processing unit 32 (step S20). When the infrared laser beam 50b is emitted in the plurality of frames, the image generation unit 33 may generate the examination image by calculating an average value of output signals from the detector 40 in the respective frames, or may generate the examination image based on a maximum value of the output signals. The display unit 41 displays the examination image (step S22). A doctor carefully examines the examination image indicating the state of the fundus displayed on the display unit 41 to examine a visual sense of the subject. An undulating tumor, a pseudo three-dimensional image using a phase difference, the opacity of the vitreous body or the like may be detected as the detection of the state of the fundus.

Figure 5:
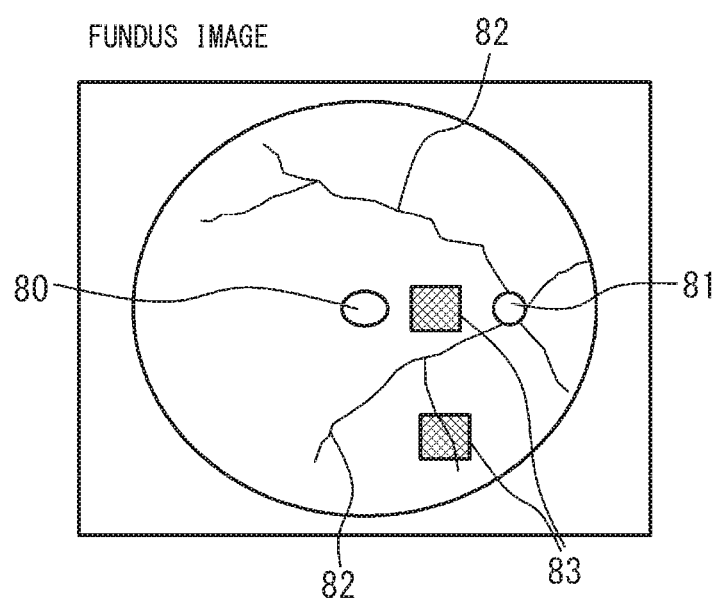
FIG. 5 is an example of a fundus image generated by an image generation unit.

FIG. 5 is an example of the fundus image generated by the image generation unit. In FIG. 5, a reference numeral 80 denotes a fovea, a reference numeral 81 denotes an optic disk, and reference numerals 82 denote retinal arteries or retinal veins. Lesions 83 are indicated by cross-hatching portions.

In the first embodiment, while the fixation visual target 63 is projected on the retina 74 of the subject, the infrared laser beam 50b is emitted to the retina 74 as illustrated in FIG. 4. This makes it possible to obtain the examination image indicating the state of the fundus in a state where the visual ne of the subject is directed to the fixation visual target 63, and thus it is possible to obtain the examination image that is stable and has good reproducibility. As described above, it is preferable that the image (e.g. the fixation visual target 63) can be projected on the retina 74 in addition to emitting to the retina 74 the infrared laser beam 50b for acquiring the examination image indicating the state of the fundus of the eye 70. However, when a liquid crystal display is used to project the image (e.g. the fixation visual target 63), it is difficult to project a high-resolution image at a predetermined position of the retina 74.

Therefore, in the first embodiment, the scanning unit 20 emits the visible laser beam 50a scanned two-dimensionally to the retina 74 to project the image (e.g. the fixation visual target 63) on the retina 74, as illustrated in FIGS. 1 and 2. Thereby, it is possible to project the high-resolution image. At this tune, it is desired that the scanning unit 20 scanning the visible laser beam 50a oscillates at about 28 kHz so that the images of 60 frames are projected per second, for example. On the other hand, when the scanning unit 22 emits the infrared laser beam alrr 50b scanned two-dimensionally to the a 74 and the state of the fundus of the subject is detected from the output signal of the detector 40 detecting a reflected beam from the retina 74, it is desired that the scanning unit 22 oscillates at about 12.5 kHz which corresponds to a case where the images of 25 frames are projected per second, for example. This is due to the convenience of the processing such as an accuracy when the infrared laser beam 50b is used. In the first embodiment, since the scanning unit 20 scanning the visible laser beam 50a and the scanning unit 22 scanning the infrared laser beam 50b are separately provided, they can oscillate at different frequencies, to thereby achieve the above-described desire. Since the scanning unit 20 emits the visible laser beam 50a scanned two-dimensionally to the retina 74 to project the image (e.g. the fixation visual target 63) on the retina 74, the size of the examination device can be reduced, as compared with the case where the image (e.g. the fixation visual target 63) is projected using the liquid crystal display. It is preferable that the scanning units 20 and 22 are two-axis MEMS mirrors from the viewpoint of reducing the size, the weight and the cost of the examination device.

According to the first embodiment, there is provided the spectral unit 13 that emits the visible laser beam 50a emitted from the beam source 11 in a first direction and emits the infrared laser beam 50b in a second direction different from the first direction, as illustrated in FIG. 2. The optical axes of the image projection optical system 14 and the infrared beam optical system 15 match each other, the image projection optical system 14 two-dimensionally scans the visible laser beam 50a emitted in the first direction by the spectral unit 13 to emit the visible laser beam 50a to the retina 74, and the infrared beam optical system 15 two-dimensionally scans the infrared laser beam 50b emitted in the second direction by the spectral unit 13 to emit the infrared laser beam 50b to the retina 74. Accordingly, the optical system from the beam source 11 to the spectral unit 13 can be shared by the visible laser beam 50a and the infrared laser beam 50b, so that the number of components can be reduced and the size of the examination device can be reduced.

In view of downsizing the examination device, the spectral unit 13 is preferably the dichroic mirror that transmits the visible laser beam 50a and reflects the infrared laser beam 50b. In contrast, the spectral unit 13 may be the dichroic mirror that reflects the visible laser beam 50a and transmits the infrared laser beam 50b. Even in this case, the examination device can be downsized.

According to the first embodiment, there is provided the synthesis unit 26 that synthesizes the visible laser beam 50a scanned by the scanning unit 20 and the infrared laser beam 50b scanned by the scanning unit 22, as illustrated in FIG. 2. This makes it easily possible to match the optical axes of the visible laser beam 50a and the infrared laser beam 50b and project their laser beams on the retina 74.

Second Embodiment

Figure 6:
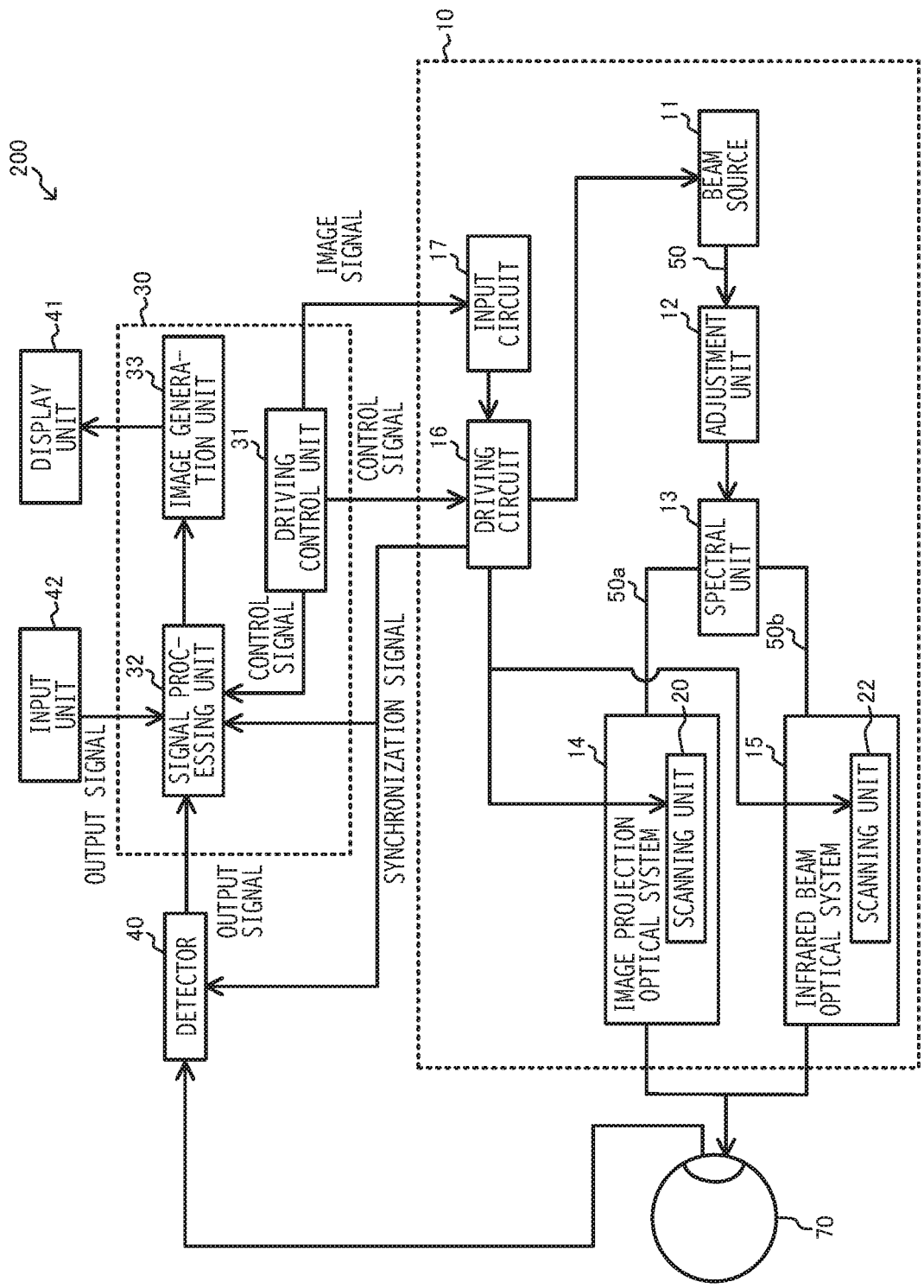
FIG. 6 is a block diagram of a visual sense examination device according to a second embodiment.

FIG. 6 is a block diagram of a visual sense examination device according to a second embodiment. As illustrated in FIG. 6, a visual sense examination device 200 according to the second embodiment further includes an input unit 42, as compared with the visual sense examination device 100 according to the first embodiment. The input unit 42 is a device to which the subject inputs results and the like, and is a button, a touch panel, a keyboard and/or a mouse, for example. The signal processing unit 32 processes the output signal of the detector 40 and an output signal of the input unit 42 based on the control signal from the driving control unit 31. The detector 40 and the signal processing unit 32 start the detection at the timing when the beam source 11 emits the visible laser beam 50a and the infrared laser beam 50b, based on the synchronization signal from the driving circuit 16. Since other configurations are the same as those in FIG. 1 of the first embodiment, the description thereof is omitted. Since the optical systems of the visual sense examination device 200 according to the second embodiment are the same as those in FIG. 1 of the first embodiment, the illustration and the description thereof are omitted.

Figure 7:
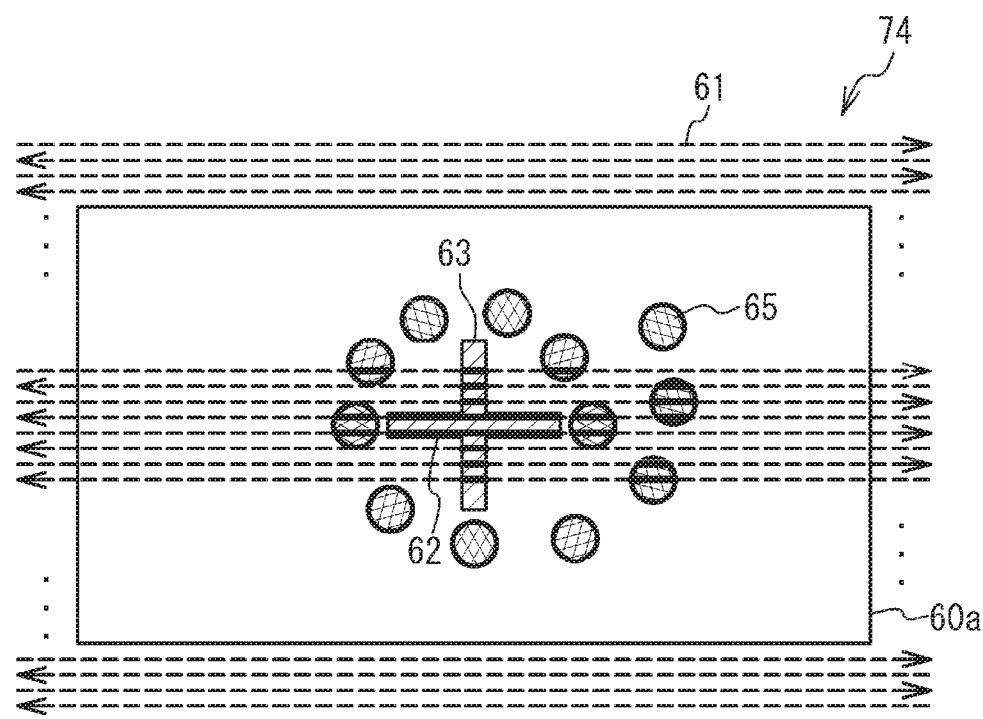
FIG. 7 is an example of an image projected on a retina according to the second embodiment.

FIG. 7 is an example of the image projected on the retina according to the second embodiment. In the second embodiment, an image 60a as illustrated in FIG. 7 is projected on the retina 74. That is, examination visual targets 65 for examining the eye 70 are projected in addition to the fixation visual target 63 projected on the central region of the retina 74. The examination visual targets 65 are projected on different regions of the retina 74 at different timings, but FIG. 7 illustrates all the examination visual targets 65 to be projected on the retina 74 for convenience. The examination visual target 65 is a stimulating beam emitted to a region with a predetermined size, for example. Although a description will be given of a case where the shape of the examination visual target 65 is a circle as an example, the shape may be an ellipse or a polygon such as a square. The examination visual target 65 may be a white beam including the red, green and blue laser beams, or may be a monochromatic beam including a laser beam with a single wavelength. The diameter of the examination visual target 65 is about several micrometers, for example.

Figure 8:
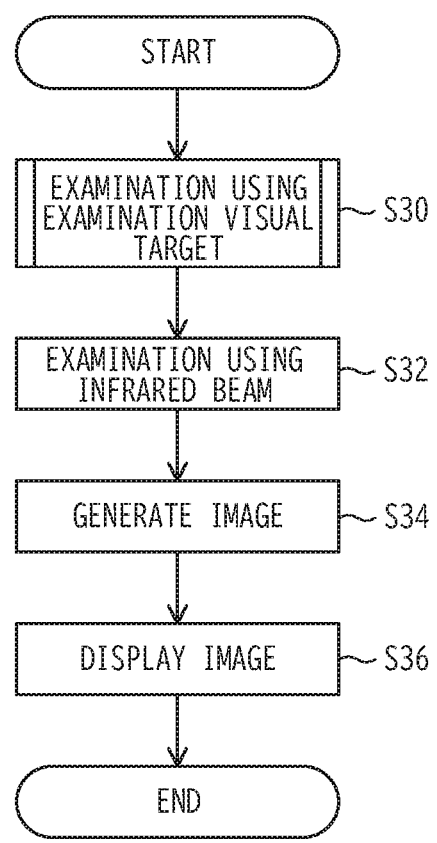
FIG. 8 is a flowchart illustrating processing according to the second embodiment.

FIG. 8 is a flowchart illustrating processing according to the second embodiment. As illustrated in FIG. 8, the control unit 30 projects an image 60a as illustrated in FIG. 7 on the retina 74, and performs the examination using the examination visual target 65 (step S30).

Figure 9:
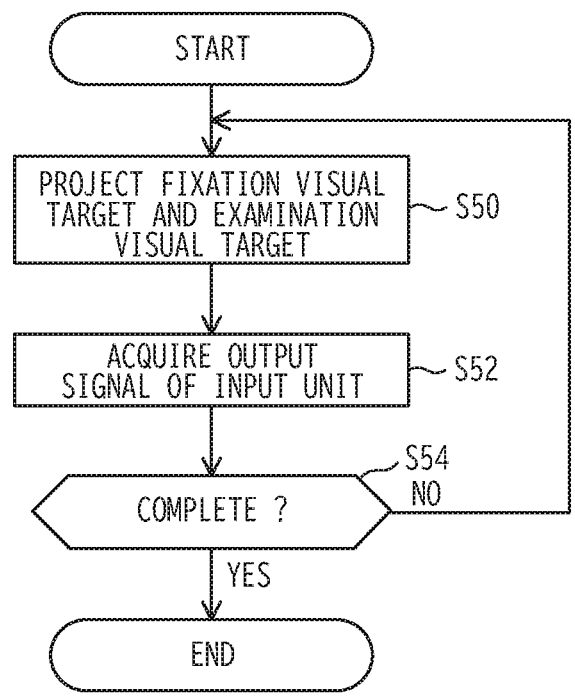
FIG. 9 is a flowchart illustrating a method of the examination using an examination visual target according to the second embodiment.
Figure 10A:
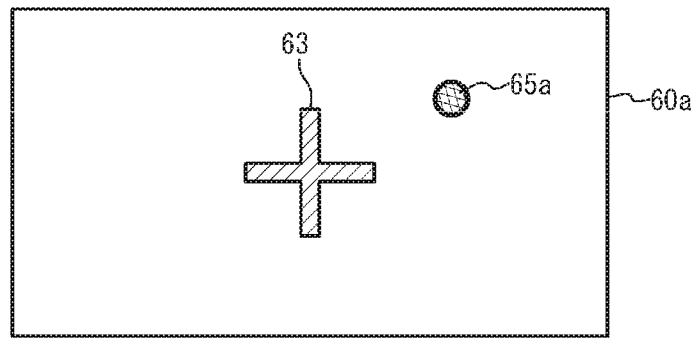
FIGS. 10A to 10D are diagrams illustrating the examination using the examination visual target.

FIG. 9 is a flowchart illustrating a method of the examination (step S30 of FIG. 8) using the examination visual target according to the second embodiment. FIGS. 10A to 10D are diagrams illustrating the examination using the examination visual target. As illustrated in FIG. 9, the driving control unit 31 generates the image 60a as illustrated in FIG. 7, causes the projection unit 10 to project the generated image 60a and further project the fixation visual target 63 and the examination visual target 65 on the retina 74 (step S50). As described with reference to FIG. 7, the examination visual targets 65 are projected on the different regions of the retina 74 at different timings. Therefore, an examination visual target 65a among the examination visual targets 65 to be projected on the different regions of the retina 74 is projected as illustrated in FIG. 10A.

Returning to FIG. 9, the signal processing unit 32 acquires the output signal of the input unit 42 (step S52). The subject operates the input unit 42 when recognizing that the examination visual target 65a is projected on the retina 74. When the subject operates the input unit 42, the output signal is output from the input unit 42 to the signal processing unit 32. The signal processing unit 32 starts acquiring the output signal of the input unit 42 in synchronization with the emission of the visible laser beam 50a.

Figure 10B:
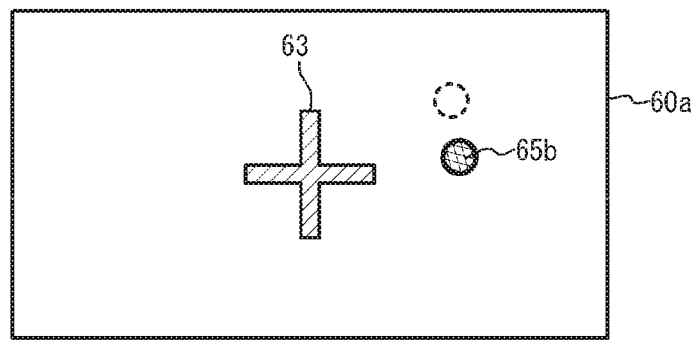
Figure 10C:
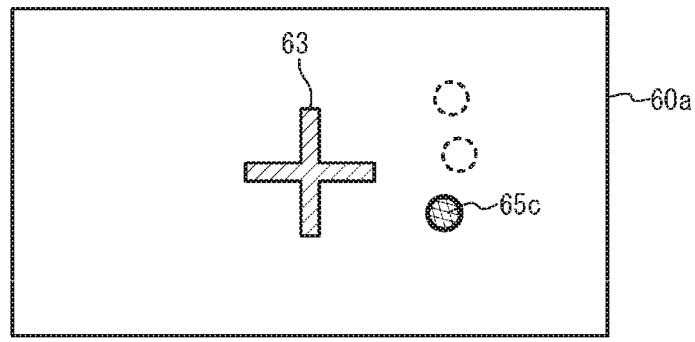
Figure 10D:
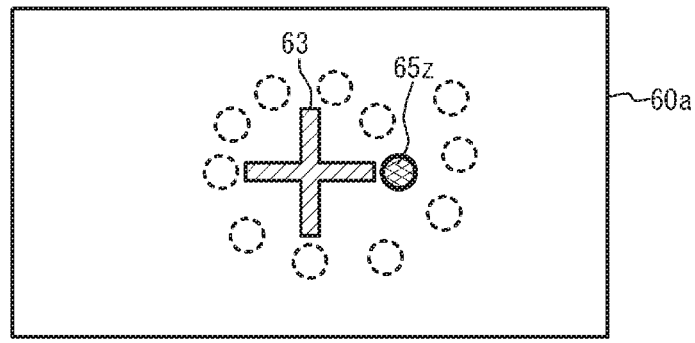

Next, the driving control unit 31 determines whether the projection of all the examination visual targets 65 on the retina 74 has completed (step S54). When the examination visual target 65 to be projected still remains, the determination in step S54 is denied (step S54: No), and steps S50 and S52 are repeatedly performed. When steps S50 and S52 are repeatedly performed, for example, the examination visual target 65a of FIG. 10A is projected and several seconds elapse, an examination visual target 65b is then projected on another region of the retina 74 as illustrated in FIG. 10B and several seconds further elapse, and then an examination visual target 65c is projected on still another region of the retina 74 as illustrated in FIG. 10C. This is repeatedly performed, and a final examination visual target 65z is projected on the retina 74, as illustrated in FIG. 10D. When the projection of all the examination visual targets 65 has completed (step S54: Yes), the examination using the examination visual targets 65 completes. Thereby, the examination for the visual field defect can be performed, for example.

Returning to FIG. 8, the control unit 30 detects the state of the fundus using the infrared laser beam 50b (step S32). In the detection of the state of the fundus using the infrared laser beam 50b, the processing of steps S10 to S18 in FIG. 4 is performed.

Next, the image generation unit 33 generates the visual field defect image based on the output signal of the input unit 42 obtained by the signal processing unit 32 in the examination using the examination visual target 65. The image generation unit 33 generates a fundus image based on the output signal of the detector 40 obtained by the signal processing unit 32 by emitting the infrared laser beam 50b (in the examination using the infrared laser beam 50b). Then, the image generation unit 33 generates the superimposed image in which the visual field defect image and the fundus image are superimposed (step S34). The display unit 41 displays the superimposed image (step S36). The doctor carefully examines the examination image displayed in a superimposed fashion on the display unit 41 to examine the visual sense of the subject.

Figure 11A:
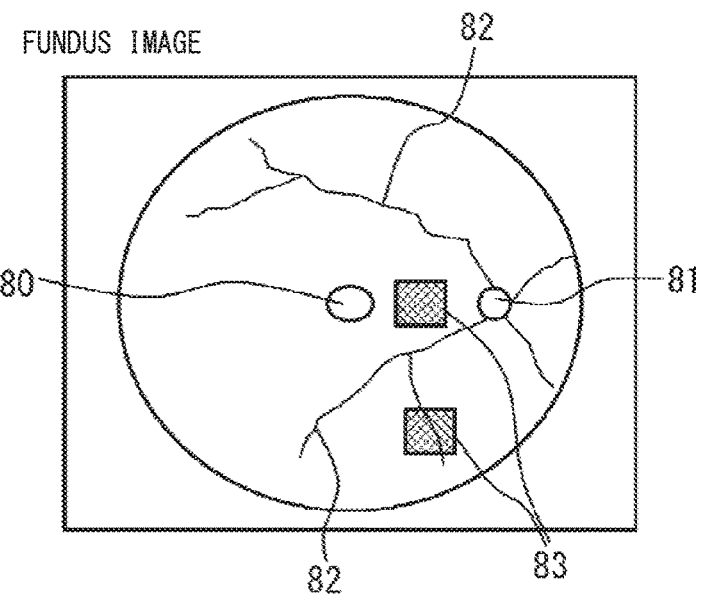
FIGS. 11A to 11C are examples of the fundus image, a visual field defect image and a superimposed image generated by the image generation unit.
Figure 11B:
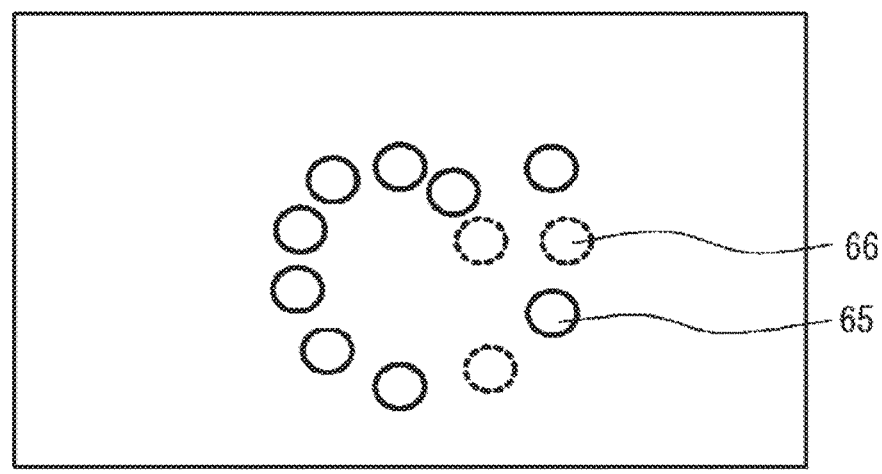
Figure 11C:
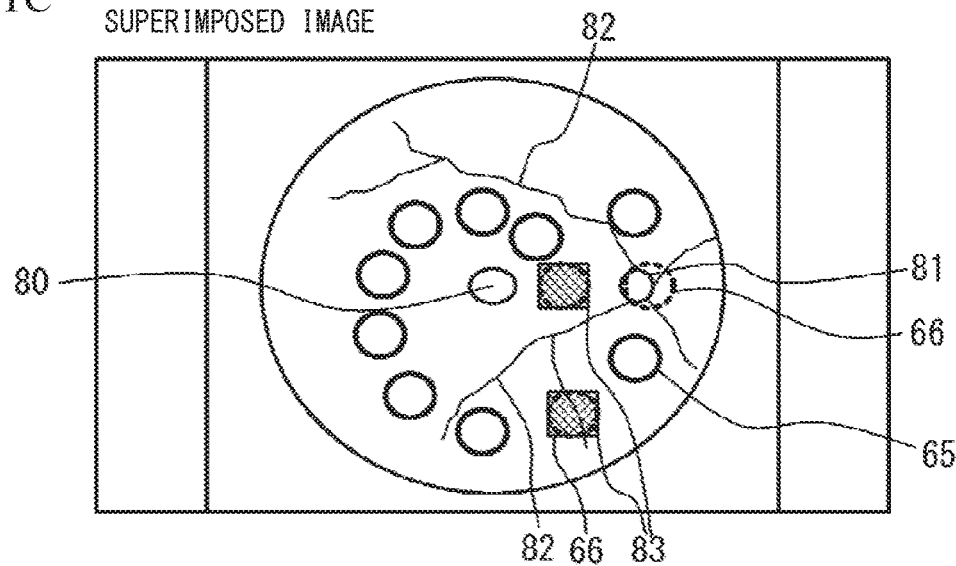

FIGS. 11A to 11C are examples of the fundus image, the visual field defect image and the superimposed image generated by the image generation unit. FIG. 11A illustrates the fundus image. As with FIG. 5, the reference numeral 80 denotes the fovea, the reference numeral 81 denotes the optic disk, and the reference numerals 82 denote the retinal arteries or retinal veins. The lesions 83 are indicated by the cross-hatching portions. FIG. 11B illustrates the visual field defect image. Dotted lines indicate parts 66 where the subject has not input a response to the input unit 42 even though the examination visual target 65 has been projected on the retina 74. FIG. 11C illustrates the superimposed image in which the fundus image and the visual field defect image are superimposed. By superimposing the fundus image and the visual field defect image, it is possible to evaluate a relationship between the lesions 83 in the fundus image and the visual field defect parts 66 in the visual field defect image.

According to the second embodiment, the control unit 30 controls the emission of the visible laser beam 50a from the beam source 11 and projects the examination visual target 65 for examining the eye 70 on the retina 74 of the subject. Thereby, the examination of the eye 70 can be performed using the visible laser beam 50a in addition to detecting the state of the fundus of the eye 70 using the infrared laser beam 50b.

FIG. 8 illustrates that the examination using the infrared laser beam 50b is performed after the examination using the examination visual target 65 is performed. But, the examination visual target 65 may be performed after the examination using the infrared laser beam 50b is performed. In this case, when the examination using the examination visual target 65 is performed, the visible laser beam 50a is emitted from the beam source 11 and the scanning unit 20 is driven, and the infrared laser beam 50b does not have to be emitted from the beam source 11 and the scanning unit 22 does not have to be driven. When the examination using the infrared laser beam 50b is performed, the infrared laser beam 50b is emitted from the beam source 11 and the scanning unit 22 is driven, and the visible laser beam 50a does not have to be emitted from the beam source 11 and the scanning unit 20 does not have to be driven. Also, the examination using the examination visual target 65 and the examination using the infrared laser beam 50b may be performed in parallel. That is, the control unit 30 may simultaneously perform the projection of the examination visual target 65 and the emission of the infrared laser beam 50b in parallel. Thereby, the examination time can be reduced.

According to the second embodiment, the control unit 30 generates the superimposed image in which the examination image (the fundus image) generated based on the output signal of the detector 40 and the examination image (the image related to the visual field defect) generated based on the output signal of the input unit 42 are superimposed, as illustrated in FIG. 11C. This makes it possible to evaluate the relationship between the lesion in the examination image of the examination using the visible laser beam 50a and the lesion in the examination image of the examination using the infrared laser beam 50b. Further, this makes it possible to contribute to early detection of onset of diabetes, early detection of glaucoma, and/or early detection of age-related macular degeneration. Also, by generating the image related to the visual field defect, PRL (Preferred Retinal Locus: another retinal region that captures a visual object instead of the retinal fovea due to the reduction of the sensitivity of the retinal fovea) can also be specified.

Figure 12A:
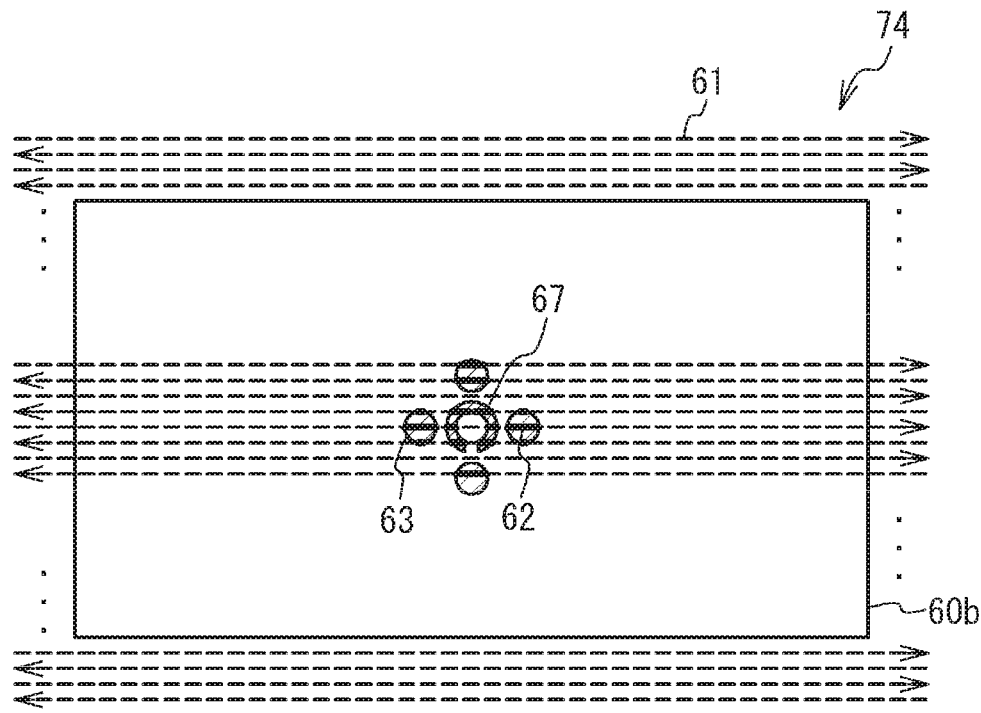
FIGS. 12A and 12B are other examples of images projected on the retina according to the second embodiment.
Figure 12B:
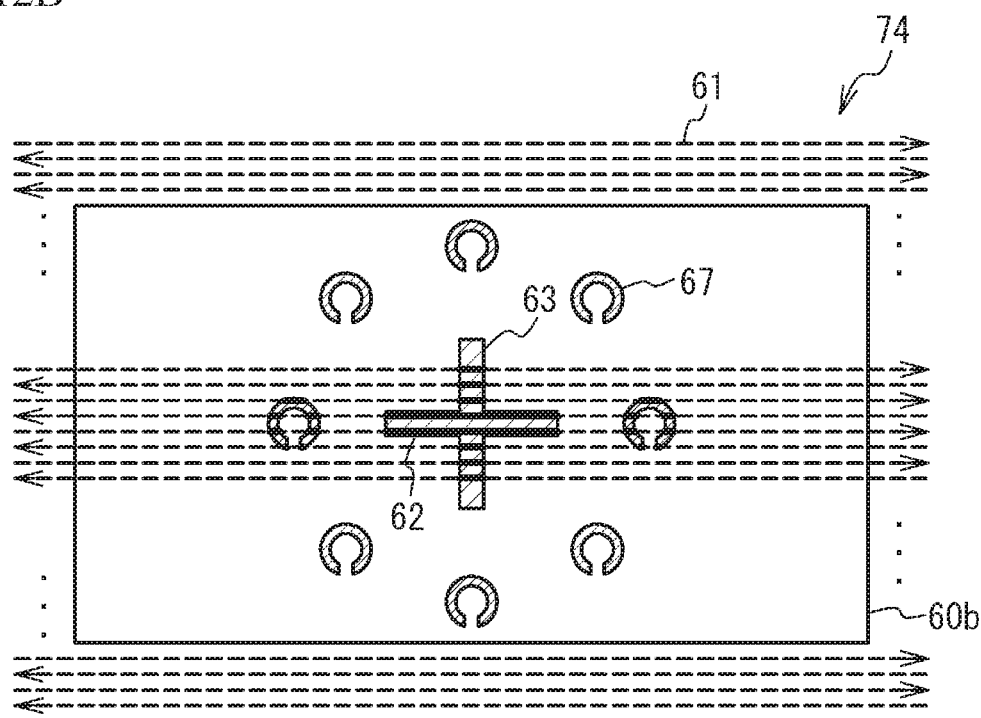

The second embodiment illustrated a case where the examination image generated based on the output signal of the detector 40 is the fundus image, and the examination image generated based on the output signal of the input unit 42 is the image related to visual field defect. However, the examination images may be other examples. FIGS. 12A and 12B are other examples of images projected on the retina according to the second embodiment. As illustrated in FIGS. 12A and 12B, an image 60b having an examination visual target 67 for examining retinal visual acuity may be projected on the retina 74. That is, an image of an examination result of the retinal visual acuity may be generated based on the output signal of the input unit 42. As illustrated in FIG. 12A, the examination visual target 67 is projected at the center of the image 60b, and a plurality of dot patterns are projected as the fixation visual target 63 so as to surround the examination visual target 67. Thereby, when the subject looks at the plurality of fixation visual targets 63 uniformly, the examination visual target 67 is projected on the center of the retina 74. As illustrated in FIG. 12B, the fixation visual target 63 is projected at the center of the image 60b, and the examination visual targets 67 are projected around the fixation visual target 63. As with FIG. 7, the examination visual targets 67 are projected on different regions of the retina 74 at different timings, but FIG. 12B illustrates all the examination visual targets 67 to be projected on the retina 74 for convenience. Thereby, when the subject looks at the fixation visual target 63, the examination visual target 67 is projected at a desired position of the retina 74. Thus, when the examination visual target 67 is projected, the fixation visual target 63 is also projected and the eye of the subject is fixated on the fixation visual target 63, which makes it possible to project the examination visual target 67 at the desired position of the retina 74. Here, the examination visual target 67 is not limited to the Landolt ring, but may be other marks such as characters.

In the first and the second embodiments, the image projection optical system 14 projects the fixation visual target 63 and the infrared beam optical system 15 emits the infrared laser beam 50b to the retina 74, so that the control unit 30 can acquire the image in which the fixation visual target 63 is displayed on the examination image of the eye 70 by the infrared laser beam 50b. Thereby, when the examination images of the plurality of frames are acquired, the alignment of the images can be easily performed by the fixation visual target 63 on the examination image. Also, even when the visual line of the subject moves despite projecting the fixation visual target, it is possible to more accurately perform the superimposition of the examination images of the frames, the specification of the position of the lesion, and so on.

Third Embodiment

The first and the second embodiments illustrated a case where the image projection optical system 14 projects the image such as the visual target, and the infrared beam optical system 15 detects the state of the fundus of the eye 70 of the subject with the infrared laser beam 50b emitted to the retina 74. In a third embodiment, a description will be given of a case where the image projection optical system 14 also detects the state of the fundus of the eye 70 of the subject with the visible laser beam 50a emitted to the retina 74.

Since the block diagram and the optical system of the visual sense examination device according to the third embodiment are the same as those in FIGS. 1 and 2 of the first embodiment, the description thereof will be given with reference to FIGS. 1 and 2 of the first embodiment. The visual sense examination device of the third embodiment differs from that of the first embodiment in that the detector 40 is a photodetector capable of detecting the visible beam and the infrared beam. Therefore, in the third embodiment, the image projection optical system 14 emits the visible laser beam 50a to the retina 74, and the detector 40 can detect the visible laser beam 50a reflected by the retina 74. The visible laser beam 50a reflected by the retina 74 returns in an order of the lens 27, the synthesis unit 26, the lens 25, the scanning unit 20, the plane mirror 21 and the spectral unit 13, along the optical path where the visible laser beam 50a has advanced toward the retina 74. Then, the visible laser beam 50a enters the detector 40 via the half mirror 43 and the lens 44.

Figure 13:
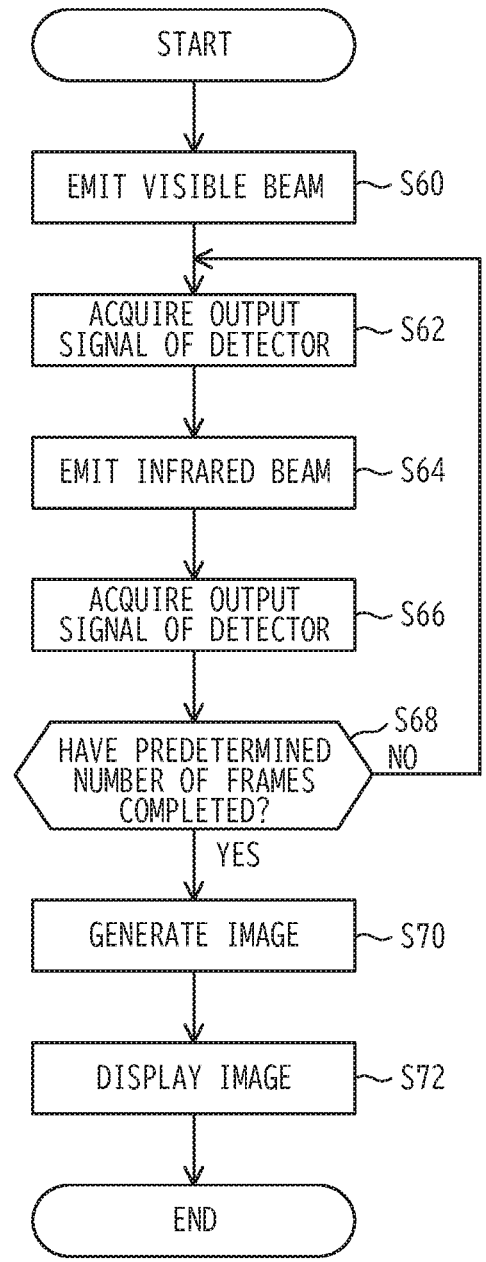
FIG. 13 is a flowchart illustrating processing according to a third embodiment.

FIG. 13 is a flowchart illustrating processing according to the third embodiment. As illustrated in FIG. 13, the driving control unit 31 causes the projection unit 10 to emit the visible laser beam 50a to the retina 74 (step S60). Next, the signal processing unit 32 acquires the output signal of the detector 40 (step S62). For example, the detector 40 detects the visible laser beam 50a in synchronization with the synchronization signal from the driving circuit 16. That is, the detector 40 detects the visible laser beam 50a in synchronization with the emission of the visible laser beam 50a from the beam source 11. The signal processing unit 32 starts acquiring the output signal of the detector 40 in synchronization with the emission of the visible laser beam 50a.

Next, the driving control unit 31 causes the projection unit 10 to emit the infrared laser beam 50b to the retina 74 instead of the visible laser beam 50a (step S64). Next, the signal processing unit 32 acquires the output signal of the detector 40 (step S66). For example, the detector 40 detects the infrared laser beam 50b in synchronization with the synchronization signal from the driving circuit 16. That is, the detector 40 detects the infrared laser beam 50b in synchronization with the emission of the infrared laser beam 50b from the beam source 11. The signal processing unit 32 starts acquiring the output signal of the detector 40 in synchronization with the emission of the infrared laser beam 50b.

Next, the driving control unit 31 determines whether the emission of the visible laser beam 50a and the infrared laser beam 50b corresponding to a predetermined number of frames has completed (step S68). The predetermined number of frames may be one frame or the plurality of frames such as 5 frames or 10 frames.

When the emission corresponding to the predetermined number of frames has not completed (step S68: No), steps S60 to S66 are repeatedly performed. When the emission corresponding to the predetermined number of frames has completed (step S68: Yes), the image generation unit 33 generates the examination images of the eye 70 based on the output signal of the detector 40 acquired by the signal processing unit 32 (step S70). For example, the image generation unit 33 may generate a first examination image (a first fundus image) based on the output signal of the detector 40 corresponding to the visible laser beam 50a reflected by the retina 74, and generate a second examination image (a second fundus image) based on the output signal of the detector 40 corresponding to the infrared laser beam 50b reflected by the retina 74. The display unit 41 displays the examination images (step S72). The doctor carefully examines the examination images displayed on the display unit 41 to examine the visual sense of the subject.

According to the third embodiment, the control unit 30 detects the state of the fundus of the eye 70 from the output signal of the detector 40 based on the infrared laser beam 50b, and detects the state of the fundus of the eye 70 from the output signal of the detector 40 based on the visible laser beam 50a. Since the two detected state of the fundus are based on laser beams having different frequencies, it is possible to detect the states of the fundus having different characteristics. This makes it possible to evaluate different states of the fundus and improve the accuracy of the visual examination.

The third embodiment illustrated a case where the fundus images of the eye 70 are acquired as an example of detecting the states of the fundus of the eye 70 from the output signals of the detector 40 based on the visible laser beam 50a and the infrared laser beam 50b. However, a method of detecting the states of the fundus may be another method.

Also in the third embodiment, the control unit 30 may project the fixation visual target for directing the visual line of the subject on the retina 74 of the subject as in the first embodiment, and/or may project the examination visual target for examining the eye 70 of the subject on the retina 74 of the subject as in the second embodiment.

Fourth Embodiment

The first to the third embodiments illustrated a case where the visible laser beam 50a and the infrared laser beam 50b are two-dimensionally scanned by the separate scanning units 20 and 22, namely, a case where there is provided two types of scanning units including the scanning unit 20 that scans the visible laser beam 50a and the scanning unit 22 that scans the infrared laser beam 50b. In contrast, a fourth embodiment will describe a case where a single scanning unit performs two-dimensional scanning. That is to say, the first to the third embodiments illustrated a case where there are provided the image projection optical system 14 having the scanning unit 20 for scanning the visible laser beam 50a as visible light and the infrared beam optical system 15 having the scanning unit 22 for scanning the infrared laser beam 50b as invisible light. In contrast, the fourth embodiment will describe a case where the optical system of the visible light and the invisible light is shared, and both of the laser beams of the visible light and the invisible light are scanned by the single scanning unit.

Figure 14:
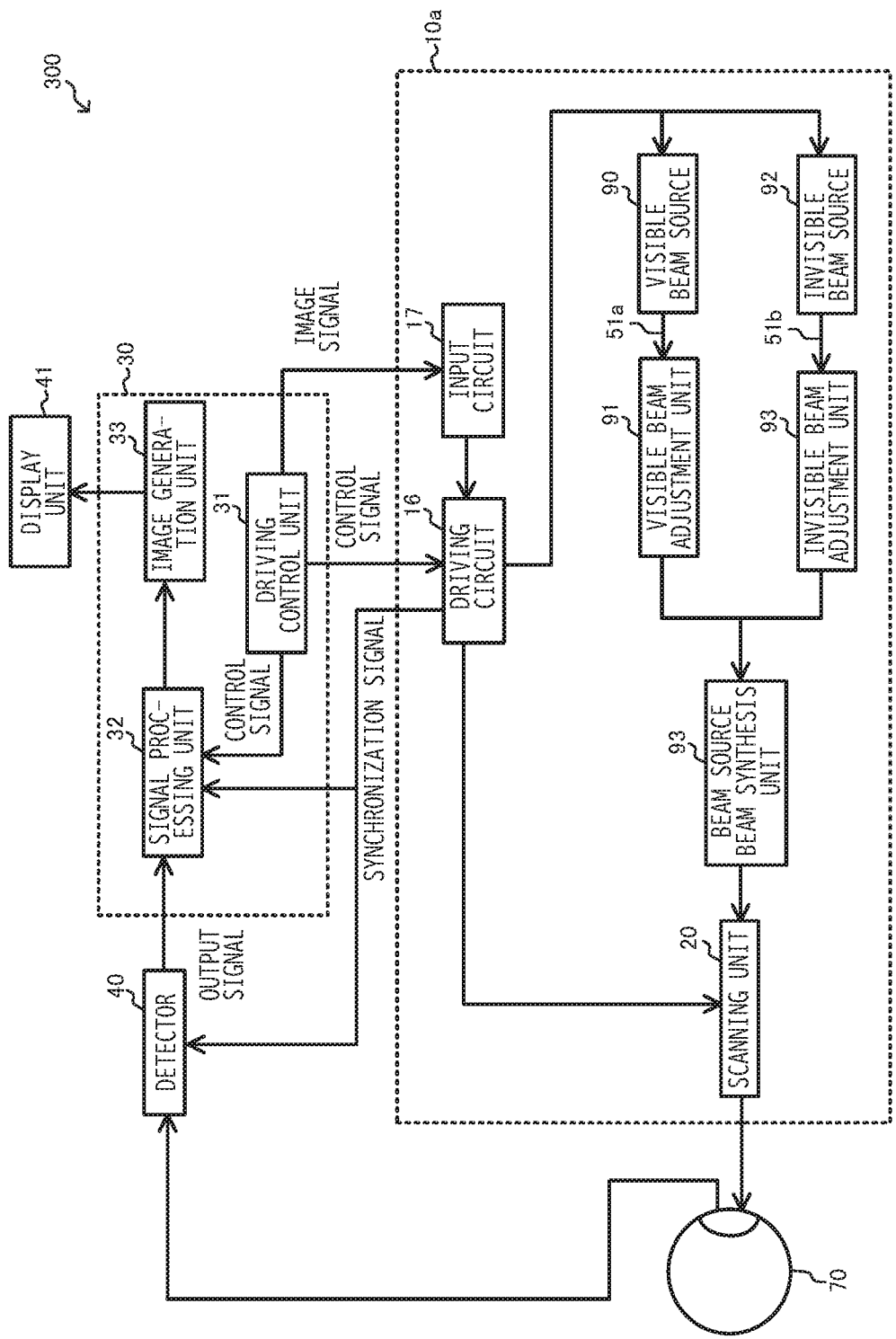
FIG. 14 is a block diagram of a visual sense examination device according to a fourth embodiment.

FIG. 14 is a block diagram of a visual sense examination device according to the fourth embodiment. In a visual sense examination device 300 according to the fourth embodiment, a projection unit 10a includes a visible beam source 90, a visible beam adjustment unit 91, an invisible beam source 92, an invisible beam adjustment unit 93, a beam source beam synthesis unit 94, the scanning unit 20, the driving circuit 16 and the input circuit 17, as illustrated in FIG. 14. The driving circuit 16 drives the visible beam source 90, the invisible beam source 92 and the scanning unit 20 based on the image signal obtained by the input circuit 17 and the control signal of the driving control unit 31. Since other configurations are the same as those in FIG. 1 of the first embodiment, the description thereof is omitted. The visual sense examination device 300 according to the fourth embodiment may include the input unit 42 as in FIG. 6 of the second embodiment.

Figure 15:
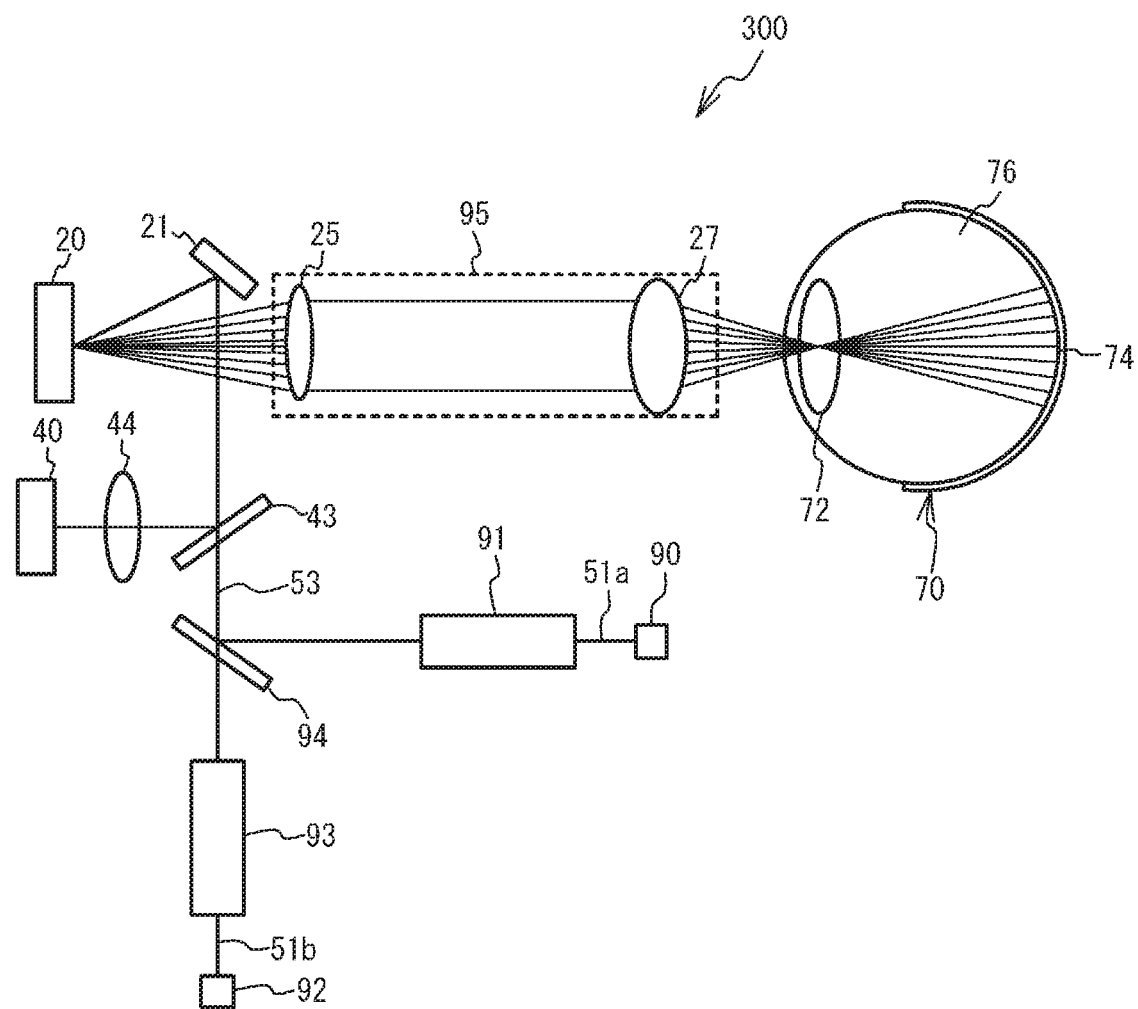
FIG. 15 is a diagram illustrating an optical system of the visual sense examination device according to the fourth embodiment.

FIG. 15 is a diagram illustrating an optical system of the visual sense examination device according to the fourth embodiment. The visual sense examination device 300 according to the fourth embodiment includes the visible beam source 90, the visible beam adjustment unit 91, the invisible beam source 92, the invisible beam adjustment unit 93 and the beam source beam synthesis unit 94, as illustrated in FIG. 15. In the fourth embodiment, the laser beam is emitted to the retina 74 of the subject using the Maxwellian view as in the first embodiment. The visible beam source 90 emits visible laser beam 51a including the red laser beam, the green laser beam and the blue laser beam, and the optical axes of the laser beams with the respective wavelengths match each other. The visible beam adjustment unit 91 includes a collimate lens, a toric lens and/or an aperture having characteristics suitable for the visible beam, and hence the visible laser beam 51a is adjusted to a suitable numerical aperture (NA) and/or a suitable beam diameter. The visible laser beam 51a is a beam in which the red laser beam, the green laser beam and the blue laser beam are synthesized, and the optical axes of the respective laser beams match each other.

The invisible beam source 92 emits an invisible laser beam 51b such as the infrared light. The invisible beam adjustment unit 93 includes a collimate lens, a toric lens and/or an aperture having characteristics suitable for the invisible beam such as the infrared light, and hence the invisible laser beam 51b is adjusted to a suitable numerical aperture (NA) and/or a suitable beam diameter.

The beam source beam synthesis unit 94 is a dichroic mirror that reflects the visible laser beam 51a adjusted by the visible beam adjustment unit 91, transmitting the invisible laser beam 51b adjusted by the invisible beam adjustment unit 93, whereby generating a synthesis laser beam 53 in which the adjusted visible laser beam 51a and the adjusted invisible laser beam 51b are synthesized. The beam source beam synthesis unit 94 is not limited to the dichroic mirror, but may be another optical element such as the dichroic prism.

The synthesis laser beam 53 transmits through the half mirror 43, is reflected by the plane mirror 21, and is two-dimensionally scanned by the scanning unit 20. Here, as in the first embodiment, the scanning unit 20 oscillates at a relatively high frequency such as 28 kHz so that the images of 60 frames are projected per second. The synthesis laser beam 53 scanned by the scanning unit 20 converges near the crystalline lens 72 via the lens 25 and the lens 27, passes through the vitreous body 76, and is emitted to the retina 74. The lens 25 and the lens 27 become an emission optical system 95 that emits the visible laser beam 51a to the retina 74 of the subject to project the image on the retina 74 of the subject, and emits the invisible laser beam 51b to the retina 74 of the subject. Since the synthesis laser beam 53 is a laser beam in which the visible laser beam 51a and the invisible laser beam 51b are mixed, in the fourth embodiment, the visible laser beam 51a and the invisible laser beam 51b are simultaneously emitted to the same position of the retina 74 at the same scanning frequency.

The synthesis laser beam 53 emitted to the retina 74 is reflected by the retina 74. The reflected synthesis laser beam 53 returns along the optical path where the synthesis laser beam 53 has advanced toward the retina 74. That is, the reflected synthesis laser beam 53 returns in an order of the lens 27, the lens 25, the scanning unit 20 and the plane mirror 21, along the optical path where the synthesis laser beam 53 has advanced toward the retina 74. The returned synthetic laser beam 53 is reflected by the half mirror 43 in a direction of the lens 44, and enters the detector 40 via the lens 44. Since the detector 40 has a characteristic of detecting the invisible beam and not detecting the visible beam, the detector 40 detects only the reflected invisible laser beam 51b. The state of the fundus of the eye 70 can be detected (i.e., state information of the fundus can be acquired) based on the detection result of the luminance change of the invisible laser beam 51b by the detector 40, and the fundus image can be acquired as an example of the detection object. When the detector 40 has a characteristic capable of detecting both of the visible beam and the invisible beam, if the detection result detected by the detector 40 is referred to in accordance with the emission timing of the visible laser beam 51a and the invisible laser beam 51b, both of the visible laser beam 51a and the invisible laser beam 51b can be detected.

The method of the scanning and the projection of the visible laser beam and the invisible laser beam illustrated in FIGS. 3, 7, 10 and 12, and the processing control flowchart illustrated in FIGS. 4, 8, 9 and 13 according to the first to the third embodiments are applied as the method of the scanning and projection and the control flowchart according to the fourth embodiment, by replacing the visible laser beam 50a and the infrared laser beam 50b with the visible laser beam 51a and the invisible laser beam 51b.

According to the fourth embodiment, the synthetic laser beam 53 obtained by synthesizing the visible laser beam 51a and the invisible laser beam 51b by the beam source beam synthesis unit 94 is scanned by the single scanning unit 20 and emitted to the retina 74 of the subject. Thus, since the scanning unit 20 that scans the visible laser beam 51a and the invisible laser beam 51b is shared, the control of the scanning unit 20 can be simplified, and the simplification of the device can be also realized.

The first to the fourth embodiment illustrated the infrared beam as the invisible beam, but the invisible beam may be another beam such as an ultraviolet beam. The first to the fourth embodiment illustrated a case where the wavelength of the infrared beam is about 850 nm, but a near-infrared beam with another wavelength may be used. Also, a middle-infrared beam or a far-infrared beam may be used.

Although embodiments of the present invention have been specifically described, the present invention is not limited to those particular embodiments, and various changes and modifications may be made to them without departing from the scope of the invention disclosed in the claims.

DESCRIPTION OF REFERENCE NUMERALS 10, 10a projection unit
11 beam source
12 adjustment unit
13 spectral unit
14 image projection optical system
15 infrared beam optical system
16 driving circuit
17 input circuit
20, 22 scanning unit
21, 23 plane mirror
24, 25, 27 lens
26 synthesis unit
30 control unit
31 driving control unit
32 signal processing unit
33 image generation unit
40 detector
41 display unit
42 input unit
43 half mirror
44 lens
50 laser beam
50a visible laser beam
50b infrared laser beam
51a visible laser beam 51b invisible laser beam
53 synthesis laser beam
60-60b image
63 fixation visual target
65-65z examination visual target
66 part
67 examination visual target
70 eye
72 crystalline lens
74 retina
76 vitreous body
80 fovea
81 optic disk
82 retinal artery or retinal vein
83 lesion
90 visible beam source
91 visible beam adjustment unit
92 invisible beam source
93 invisible beam adjustment unit
94 beam source beam synthesis unit
95 emission optical system
100, 200, 300 visual sense examination device

The invention claimed is:

1. A visual sense examination device, comprising:
a beam source that emits a visible beam and an invisible beam;
a visible beam optical system that includes a first scanner two-dimensionally scanning the visible beam, and that emits the visible beam to a retina of a subject;
an invisible beam optical system that includes a second scanner two-dimensionally scanning the invisible beam, and that emits the invisible beam to the retina of the subject;
a detector that detects the invisible beam reflected by the retina of the subject;
a controller that performs a first control, the first control including:
controlling the emission of the visible beam from the beam source, and causing the first scanner to scan the visible beam for an image for projecting the image and to emit the visible beam for the image to the retina of the subject;
controlling the emission of the invisible beam from the beam source, and causing the second scanner to scan the invisible beam for detecting a state of a fundus of the subject and to emit the invisible beam to the retina of the subject; and
acquiring a first fundus image of an eye of the subject from an output signal of the detector based on the invisible beam for detecting the state of the fundus of the subject;
synthesizer that synthesizes the visible beam scanned by the first scanner and the invisible beam scanned by the second scanner; and
wherein a scanning angle of the visible beam by the first scanner and a scanning angle of the invisible beam by the second scanner are substantially the same,
an angle of emission from the synthesizer of the visible beam scanned two-dimensionally by the first scanner and an angle of emission from the synthesizer of the invisible light scanned two-dimensionally by the second scanner are substantially the same, and
a projectable range of the visible beam scanned two-dimensionally by the first scanner and a projectable range of the invisible light scanned two-dimensionally by the second scanner are substantially the same on the retina of the subject.

2. The visual sense examination device according to claim 1, wherein the visible beam optical system and the invisible beam optical system share a first lens that is disposed between the synthesizer and the eye of the subject, and converges the visible beam scanned by the first scanner and the invisible beam scanned by the second scanner inside the eye of the subject,
the visible beam optical system includes a second lens disposed between the first scanner and the synthesizer, and guiding the visible beam scanned by the first scanner to the synthesizer, and
the invisible beam optical system includes a third lens disposed between the second scanner and the synthesizer, and guiding the invisible beam scanned by the second scanner to the synthesizer.

3. The visual sense examination device according to claim 1, comprising:
a spectroscope that emits the visible beam emitted from the beam source in a first direction, and emits the invisible beam emitted from the beam source in a second direction different from the first direction;
wherein the visible beam optical system two-dimensionally scans the visible beam emitted in the first direction to emit the visible beam to the retina of the subject,
the invisible beam optical system two-dimensionally scans the invisible beam emitted in the second direction to emit the invisible beam to the retina of the subject,
the detector detects the invisible beam reflected by the retina of the subject, the invisible beam passing through the synthesizer, the second scanner and the spectroscope.

4. The visual sense examination device according to claim 3, wherein the spectroscope is a dichroic minor that transmits one of the visible beam and the invisible beam, and reflects the other thereof.

5. The visual sense examination device according to claim 1, wherein the invisible beam is an infrared beam.

6. The visual sense examination device according to claim 1, wherein when the controller causes the beam source to emit the invisible beam for detecting the state of the fundus of the subject, the controller projects, on the retina of the subject, a fixation visual target for directing a visual line of the subject by the visible beam for the image.

7. The visual sense examination device according to claim 1, wherein the controller projects an examination visual target for examining an eye of the subject on the retina of the subject by the visible beam for the image.

8. The visual sense examination device according to claim 7, wherein the controller performs the projection of the examination visual target and the emission of the invisible beam in parallel.

9. The visual sense examination device according to claim 7, wherein the controller projects a visual target for examining a visual field of the subject, as the examination visual target.

10. The visual sense examination device according to claim 9, wherein the controller generates a superimposed image in which the first fundus image and a visual field defect image are superimposed, the visual field defect image being generated based on a response input in accordance with the examination visual target of the subject.

11. The visual sense examination device according to claim 1, wherein the detector detects a visible beam for fundus examination for detecting the state of the fundus of the subject, and the invisible beam reflected by the retina of the subject, the visible beam for fundus examination being reflected by the retina of the subject and different from the visible beam for the image, the controller performs a second control, the second control including:

controlling the emission of the visible beam from the beam source to emit the visible beam for fundus examination to the retina of the subject;

controlling the emission of the invisible beam from the beam source to emit the invisible beam for detecting the state of the fundus of the subject to the retina of the subject;

acquiring a second fundus image of the eye of the subject from the output signal of the detector based on the visible beam for fundus examination; and acquiring a third fundus image of the eye of the subject from the output signal of the detector based on the invisible beam for detecting the state of the fundus of the subject.

12. The visual sense examination device according to claim 3, wherein optical axes of the visible beam and the invisible beam from the beam source to the spectroscope match, and the optical axes thereof from the spectroscope to the retina of the subject match.

13. The visual sense examination device according to claim 1, wherein the visible beam optical system and the invisible beam optical system share the synthesizer and a first lens, the synthesizer is disposed in an optical path of the visible beam and the invisible beam between the first and second scanner and an eye of the subject, the first lens that is disposed between the synthesizer and the eye of the subject and converges the visible beam scanned by the first scanner and the invisible beam scanned by the second scanner inside the eye of the subject, and the visible beam scanned by the first scanner and the invisible beam scanned by the second scanner enter the same area of the first lens.

\* \* \* \* \*